United States Patent [19]

Takemoto et al.

[11] 4,129,436
[45] Dec. 12, 1978

[54] N'-[4-(SUBSTITUTED PHENETHYLOXY)PHENYL]-N-METHYL-N-METHOXYUREA

[75] Inventors: Ichiki Takemoto, Toyonaka; Ryo Yoshida, Kawanishi; Seizo Sumida, Nishinomiya; Katsuzo Kamoshita, Osaka, all of Japan

[73] Assignee: Sumitomo Chemical Company, Limited, Osaka, Japan

[21] Appl. No.: 882,383

[22] Filed: Mar. 1, 1978

[30] Foreign Application Priority Data

Mar. 3, 1977 [JP] Japan .................................. 52-23443

[51] Int. Cl.$^2$ ..................... A01N 9/20; C07C 69/76
[52] U.S. Cl. ................... 71/120; 260/453 RW
[58] Field of Search ................... 260/453 RW; 71/120

[56] References Cited

U.S. PATENT DOCUMENTS

| | | | |
|---|---|---|---|
| 2,655,447 | 10/1953 | Todd | 260/453 RW |
| 3,198,830 | 8/1965 | Scherer et al. | 260/453 RW |
| 3,746,532 | 7/1973 | Kimura et al. | 71/120 |
| 3,819,697 | 6/1974 | Cross | 260/553 A |
| 3,937,726 | 2/1976 | Scherer et al. | 71/120 |
| 3,972,909 | 8/1976 | Kubo et al. | 71/120 |

FOREIGN PATENT DOCUMENTS 507646 7/1971 Switzerland.
532891 3/1973 Switzerland.

OTHER PUBLICATIONS

Morrison and Boyd, Organic Chemistry, 3rd edition, 1973, p. 556.
Andersen, "Weed Science", vol. 19, Issue 3 (May) pp. 219-222 (1971).

*Primary Examiner*—Elbert L. Roberts
*Assistant Examiner*—Robert C. Whittenbaugh
*Attorney, Agent, or Firm*—Birch, Stewart, Kolasch and Birch

[57] ABSTRACT

An N'-[4-(substituted phenethyloxy)phenyl]-N-methyl-N-methoxyurea of the formula:

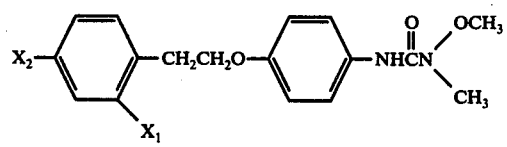

wherein $X_1$ is a hydrogen atom or a methyl group and $X_2$ is a $C_1$–$C_5$ alkyl or a $C_1$–$C_5$ alkoxy group, which shows a pronounced herbicidal activity against a wide variety of weeds in the cultivation of soybean, peanut, cotton, corn, wheat or rice plants without any material toxicity to mammals, fishes and said crop plants.

7 Claims, No Drawings

N'-[4-(SUBSTITUTED PHENETHYLOXY)PHENYL]-N-METHYL-N-METHOXYUREA

The present invention relates to N'-[4-(substituted phenethyloxy)phenyl]-N-methyl-N-methoxyureas (hereinafter referred to as "substituted urea(s)") of the formula:

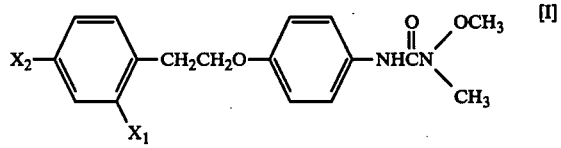

wherein $X_1$ is a hydrogen atom or a methyl group and $X_2$ is a $C_1$-$C_5$ alkyl (e.g. methyl, ethyl, propyl, butyl, pentyl) or a $C_1$-$C_5$ alkoxy group (e.g. methoxy, ethoxy, propoxy, butoxy, pentoxy), and their preparation and use.

As is well known, soybean, peanut, cotton, corn, wheat, rice and the like are crops of world-wide importance. In cultivation of the said crop plants, chemical control of weeds is indispensable to prevent yield reduction.

Among substituted urea derivatives, as is well known, there are compounds having a strong herbicidal activity such as N'-4-chlorophenyl-N,N-dimethylurea (monuron) and N'-3,4-dichlorophenyl-N,N-dimethylurea (diuron). It is also well known that the herbicidal activity of these urea derivatives is due to the inhibition of photosynthesis. Photosynthesis is a physiological function peculiar to higher plants and is not operative in mammals. Accordingly, it is highly possible that specific inhibitors of photosynthetic processes do no significant damage to mammals but can exterminate higher plants. In fact, herbicidal photosynthesis inhibitors such as monuron, diuron, 5-bromo-3-sec-butyluracil (bromacil) and the like are all low in mammalian toxicity. However, they exert a herbicidal activity against all higher plants since photosynthesis is common to higher plants. As it is, most photosynthesis inhibitors are non-selective and do damage to crop plants. In order for a compound to be a selective herbicide, it has to have both strong herbicidal activity against weeds and a high level of selectivity to an intended crop. But, such a selective herbicide is very difficult to find and can not easily be thought out systematically be mere analogy and modification of known chemical structures. Therefore, a highly detailed study with trial and error is necessary to find such selective herbicides. For example, in the case of 2-chloro-4-ethylamino-6-isopropylamino-s-triazine (atrazine) having higher selectivity to corn, the chlorine atom at the 2-position is important to the selectivity. A compound having either a methoxy or methylthio group in place of the chlorine atom has a very low selectivity to corn [H. Gysin: "The Chemical Structure and Biological Relationship of s-Triazines" in Pesticide Chemistry, Vol. 5, pages 1 to 27 (1972)]. N'-3,4-dichlorophenyl-N-methoxy-N-methylurea (linuron) has selectivity to some crops in the Umbelliferae family such as carrot, but the compound having a methyl group in place of the methoxy group lacks the selectivity to the same plant [Herbicide Handbook of The Weed Science Society of America, 3rd Ed., pages 172 to 176 and 221 to 225 (1974)]. Selective herbicidal activity requires a very specific chemical structure, and only a slight difference in the chemical structure produces quite a large difference in degree and kind of selectivity.

The inventors chose to concentrate on phenylurea derivatives from the standpoint of low mammalian toxicity and strong herbicidal activity, and carried out an in-depth investigation on how to impart selectivity to these derivatives. As the results, it has been found that the substituted ureas [I] exhibit a strong herbicidal activity against many weeds by inhibition of photosynthesis and, besides, that they have a high selectivity to cotton, and wheat by soil application and to soybean, peanut, corn and rice by both soil and foliar applications.

In general, there are a number of selective herbicides among soil-applied herbicides, but there are only a few selective herbicides among foliar-applied herbicides. Accordingly, the outstanding property of the substituted ureas [I] lies in the fact that they have selectivity to soybean, peanut, corn and rice by foliar application and at the same time exhibit a strong herbicidal activity against a wide range of weed.

Referring to the herbicidal activity of the substituted ureas [I] in more detail, they have a strong herbicidal activity on wide ranges of upland field weeds and paddy field weeds by both pre-emergence and post-emergence applications. For example, they exhibit strong herbicidal activity, at low concentrations, on various weeds such as broad-leaved weeds, e.g. redroot pigweed (*Amaranthus retroflexus*), common lambsquarter (*Chenopodium alubum*), cocklebur (*Xanthium pennsylvanicum*), annual morningglory (*Ipomoea purpurea*), chickweed (*Stellaria media*), radish (*Raphanus sativus*), pale smartweed (*Polygonum lapathifolium*), toothcup (*Rotala indica*), pickerelweed (*Monochoria vaginalis*), false pimpernel (*Linderna pyxidaria*), pitchfork (*Bidens frondosa*), black nightshade (*Solanum nigrum*), sunflower (*Helianthus annus*), jimson weed (*Datura stramonium*), velvetleaf (*Abutilon theophrasti*), etc., grassy weeds, e.g. goose grass (*Eleusine indica*), large crabgrass (*Digitaria sanguinalis*), barnyard grass (*Echinochloa crus-galli*), green foxtail (*Setaria viridis*), etc., and sedge weeds, e.g. nutsedge (*Cyperus difformis*), etc.

As described above, the substituted ureas [I] have selectivity to cotton and wheat by soil application and to soybean, peanut, corn and rice by both soil and foliar applications. Consequently, they are useful as selective herbicides for the main crop plants such as soybean, cotton, peanut, corn, wheat, rice and the like. Further, they can be used as herbicides for pasture lands, orchards, woods and forests, and non-crop lands by taking advantage of their broad herbicidal spectra. Also, low mammalian and fish toxicity is one of the characteristics of the substituted ureas [I]. While the substituted ureas [I] are per se novel, there are some chemical-structurally related compounds known; for example, N'-(3-chloro-4-benzyloxyphenyl)-N-methoxy-N-methylurea is disclosed in Swiss Pat. No. 532,891. But, this patent gives no description on the selectivity of this compound to soybean and cotton. According to the inventors' experiments, this compound exhibits strong phytotoxicity against soybean by foliar application, as is shown in Examples I and V hereinafter presented.

One of the greatest characteristics of the substituted ureas [I] consists in that they can be used as selective foliar-applied herbicides over the top of the soybean plants in the field. As selective foliar-applied herbicides for soybean now in practical use, there are exemplified N'-4-(4-chlorophenoxy)phenyl-N,N-dimethylurea (chloroxuron) and 3-isopropyl-1H-2,1,3-benzothiadiazine-4-(3H)-one-2,2-dioxide (bentazon). Chloroxuron tends to produce phytotoxicity to soybean so that a great care is necessary to avoid it ["Soybean Weed Control" (1974), published by Mississippi Cooperative Extension Service; "1976 Weed Control Recommendations for Mississippi" published by Mississippi State University; "Chemical Weed Control in Soybeans", OSU Extension Facts No. 2752, published by Oklahoma State University]. As is shown in the Examples hereinafter presented, the substituted ureas [I] are superior to chloroxuron in both selectivity to soybean and herbicidal activity. Bentazon has selectivity to soybean but it is poor in herbicidal activity against grassy weeds (e.g. large crabgrass, goose grass, green foxtail) as well as against some important broad-leaved weeds (e.g. annual morningglory, redroot pigweed) ["Soybean Weed Control" (1977), published by The University of Tennessee, Agricultural Extension Service]. As is clearly shown in the Examples hereinafter presented, the substituted ureas [I] have a strong herbicidal activity against large crabgrass, goose grass, green foxtail, morningglory and redroot pigweed in addition to the other important weeds so that they are clearly superior to bentazon in herbicidal spectrum. These superior properties of the substituted ureas [I] become more pronounced when they are evaluated under field conditions closely resembling those of soybean fields. The strong herbicidal activity and high selectivity to soybean plant of the substituted ureas [I] arise from the presence of the phenethyloxy moiety and the substituents in the right-hand positions on the benzene ring of the phenethyloxy moiety as shown in Formula [I]. The excellent properties of the substituted ureas [I] are the most remarkable with N'-4-[2-(4-methylphenyl)ethoxy]phenyl-N-methoxy-N-methylurea.

Due to the fact that the substituted ureas [I] are superior to chloroxuron, which is a selective herbicide for soybean now in practical use, in both selectivity and/or herbicidal activity, and the fact that the substituted ureas [I] are much superior to bentazon in the broadness of their herbicidal spectra, they are very useful for weed control in soybean fields.

The substituted ureas [I] of the present invention may be prepared by various methods, of which typical examples will be described below.

PROCEDURE A

The substituted ureas [I] can be prepared by reacting a 4-phenethyloxyphenyl isocyanate of the formula:

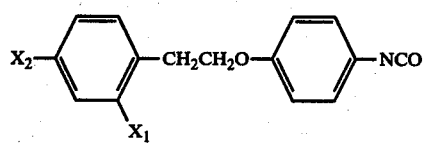

wherein $X_1$ and $X_2$ are each as defined above, with an N,O-dimethylhydroxylamine at a temperature from about $-10°$ to $150°$ C., in the presence or absence of an inert solvent (e.g. benzene, toluene, xylene, diethyl ether, tetrahydrofuran, dioxane, chloroform, carbon tetrachloride, ethyl acetate, pyridine, dimethylformamide, water or a mixture thereof) for about 10 minutes to 10 hours.

PROCEDURE B

The substituted ureas [I] can be prepared by methylating an N'-(4-phenethyloxyphenyl)-N-hydroxyurea of the formula:

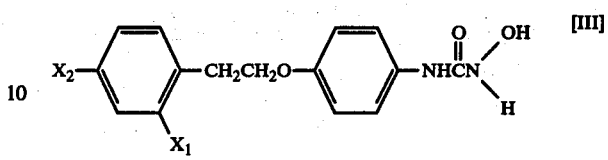

wherein $X_1$ and $X_2$ are each as defined above, with a methylating agent (e.g. methyl iodide, methyl bromide, dimethyl sulfate, diazomethane) at a temperature from about $-10°$ to $150°$ C. in the presence or absence of an inert solvent (e.g. benzene, toluene, xylene, methanol, ethanol, isopropanol, diethyl ether, tetrahydrofuran, dioxane, water or a mixture thereof), if necessary, in the presence of a base (e.g. sodium hydroxide, potassium hydroxide) for about 0.5 to 10 hours.

PROCEDURE C

The substituted ureas [I] can be prepared by reacting a 4-phenethyloxyphenylcarbamyl chloride of the formula:

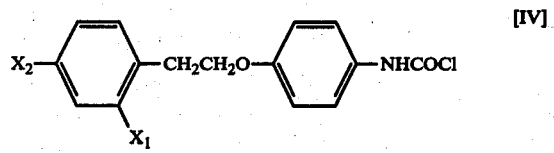

wherein $X_1$ and $X_2$ are each as defined above, with N,O-dimethylhydroxylamine at a temperature from about 0° to 150° C. in the presence or absence of an inert solvent (e.g. benzene, toluene, xylene, diethyl ether, tetrahydrofuran, dioxane, chloroform, carbon tetrachloride, ethyl acetate, pyridine, dimethylformamide or a mixture thereof), if necessary, in the presence of a dehydrochlorinating agent (e.g. pyridine, triethylamine, sodium hydroxide, potassium hydroxide, sodium carbonate) for about 0.5 to 10 hours.

PROCEDURE D

The substituted ureas [I] can be prepared by reacting a 4-phenethyloxyaniline of the formula:

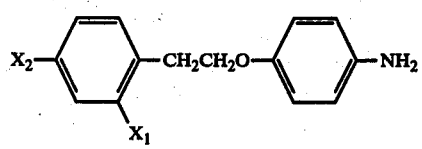

wherein $X_1$ and $X_2$ are each as defined above, with N-methyl-N-methoxycarbamyl chloride at a temperature from about 0° to 150° C. in the presence or absence of an inert solvent (e.g. benzene, toluene, xylene, diethyl ether, tetrahydrofuran, dioxane, chloroform, carbon tetrachloride, ethyl acetate, pyridine, dimethylformamide or a mixture thereof), if necessary, in the presence of a dehydrochlorinating agent (e.g. pyridine, triethylamine, sodium hydroxide, potassium hydroxide, sodium carbonate) for about 0.5 to 10 hours.

PROCEDURE E

The substituted ureas [I] can be prepared by reacting a phenethyl halide of the formula:

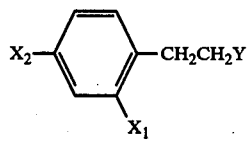

[VI]

wherein $X_1$ and $X_2$ are each as defined above and Y is a chlorine, bromine or iodine atom, with N'-(4-hydroxyphenyl)-N-methoxy-N-methylurea at a temperature from about −10° to 150° C. in an inert solvent (e.g. benzene, toluene, xylene, diethyl ether, tetrahydrofuran, dioxane, chloroform, carbon tetrachloride, ethyl acetate, methanol, ethanol, isopropanol, dimethylformamide, water or a mixture thereof), if necessary, in the presence of a dehydrochlorinating agent (e.g. pyridine, triethylamine, sodium hydroxide, potassium hydroxide, sodium carbonate) for about 0.5 to 10 hours.

The substituted ureas [I] thus produced may be purified, if necessary, by a per se conventional procedure such as recrystallization from a proper solvent.

The starting materials in the above procedures are known or may be prepared by per se conventional processes. For instance, phenethyloxyphenyl isocyanate [II] may be conveniently prepared from the corresponding readily available nitro compound as set forth below:

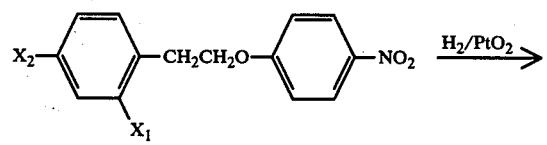

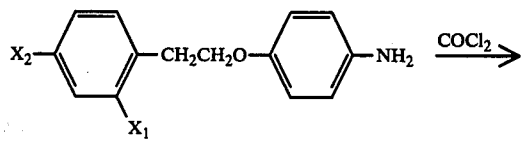

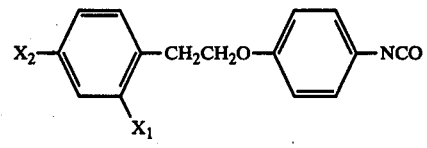

wherein $X_1$ and $X_2$ are each as defined above.

The specific examples of the substituted ureas [I] thus prepared are shown in Table 1.

Table 1

| Compound No. | Procedure | $X_1$ | $X_2$ | M.P. (° C) (or $n_D^{25}$) | Calcd. (%) C | Calcd. (%) H | Calcd. (%) N | Found (%) C | Found (%) H | Found (%) N |
|---|---|---|---|---|---|---|---|---|---|---|
| 1 | A | H | CH₃ | 82–83 | 68.77 | 7.05 | 8.91 | 68.90 | 7.20 | 8.98 |
| 2 | B | CH₃ | CH₃ | 95–95.5 | 69.47 | 7.38 | 8.58 | 69.74 | 7.48 | 8.37 |
| 3 | C | H | iso C₃H₇ | 81–82 | 70.14 | 7.67 | 8.18 | 70.40 | 7.61 | 8.36 |
| 4 | D | H | tert C₄H₉ | 14–15 | 70.76 | 7.92 | 7.86 | 71.03 | 7.91 | 7.82 |
| 5 | E | H | CH₃O | 100–101 | 65.42 | 6.72 | 8.48 | 65.36 | 6.78 | 8.44 |
| 6 | A | H | C₂H₅ | 70–71 | 69.49 | 7.37 | 8.53 | 69.19 | 7.53 | 8.16 |
| 7 | A | H | C₂H₅O | 83.5–84.0 | 66.26 | 7.02 | 8.13 | 66.21 | 7.22 | 8.07 |
| 8 | A | H | sec C₄H₉ | ($n_D^{25}$ 1.5585) | 70.76 | 7.92 | 7.86 | 70.89 | 8.08 | 7.83 |
| 9 | E | H | iso C₃H₇O | 57.0–57.5 | 67.02 | 7.31 | 7.82 | 66.93 | 7.42 | 7.84 |
| 10 | A | H | 1-methyl-butoxy | 60.5–61.0 | 68.37 | 7.82 | 7.25 | 68.14 | 8.06 | 7.22 |

Practical and presently preferred embodiments of the preparation of the substituted ureas [I] are illustratively shown in the following examples.

EXAMPLE 1

(Procedure A)

Into a solution of 5.5 g of 4-(4-methylphenethyloxy)-phenyl isocyanate in 100 ml of benzene, a solution of 2 g of N,O-dimethylhydroxylamine in 50 ml of benzene is added dropwise at 20° to 30° C. After the addition is finished, the reaction mixture is continuously stirred at the same temperature for an additional 30 minutes. Thereafter, the solvent is removed under reduced pressure, and the residue is recrystallized from ethanol to obtain 7.4 g of N'-[4-(4-methylphenethyloxy)phenyl]-N-methoxy-N-methylurea as white needles, M.P. 82°–83° C.

EXAMPLE 2

(Procedure B)

A solution of 4.7 g of 4-(2,4-dimethylphenethyloxy)-phenyl isocyanate in 50 ml of methylene chloride is added dropwise to a solution of 7 g of hydroxylamine hydrochloride and 4 g of sodium hydroxide in 15 ml of water at a temperature below 20° C. After diluting with water, the precipitated crystals are filtered and dried to obtain 4.3 g of N'-4-(2,4-dimethylphenethyloxy)phenyl-N-hydroxyurea. Into a solution of 4.3 g of the hydroxyurea derivative in 200 ml of benzene-methanol (1:1) is added dropwise 5 ml of a 10 N aqueous sodium hydroxide solution and 4 ml of dimethyl sulfate at a temperature below 30° C. After stirring at room temperature, the reaction mixture is diluted with water and extracted with benzene. The solvent is removed under reduced pressure and the residue is recrystallized from ethanol to obtain 2.1 g of N'-[4-(2,4-dimethylphenethyloxy)- phenyl]-N-methoxy-N-methylurea as white needles, M.P. 95°–95.5° C.

EXAMPLE 3

(Procedure C)

Into a solution of 10.6 g of 4-(4-isopropylphenethyloxy)phenylcarbamyl chloride in 200 ml of toluene are added 4 ml of pyridine and a solution of 2.5 g of N,O-dimethylhydroxylamine in 50 ml of toluene at a temperature below 20° C. The mixture is heated under reflux for 4 hours. The reaction mixture is then poured into ice water, and the separated organic layer is washed with dilute hydrochloric acid, thoroughly washed with water and dried over anhydrous sodium sulfate. The solvent is removed under reduced pressure, and the crude crystals are recrystallized from ethanol to obtain 4.8 g of N'-[4-(4-isopropylphenethyloxy)phenyl]-N-methoxy-N-methylurea as white needles, M.P. 81°–82° C.

EXAMPLE 4

(Procedure D)

A mixture of 26.9 g of 4-(4-tert-butylphenethyloxy)aniline, 13 g of N-methoxy-N-methylcarbamyl chloride, 10 ml of pyridine and 300 ml of toluene is heated under reflux for 7 hours. Thereafter, water is added to dissolve pyridinium chloride, and the separated toluene layer is washed with dilute hydrochloric acid, thoroughly washed with water and dried over anhydrous sodium sulfate. The solvent is then removed under reduced pressure, and the crude crystals obtained are repeatedly recrystallized from ethanol to obtain 9.3 g of N'-[4-(4-tert-butylphenethyloxy)phenyl]-N-methoxy-N-methylurea as white needles, M.P. 14°–15° C.

EXAMPLE 5

(Procedure E)

Into a solution of 8.8 g of sodium ethoxide in 200 ml of N,N-dimethylformamide is added 27 g of N'-(4-hydroxyphenyl)-N-methoxy-N-methylurea. To the mixture is added dropwise a solution of 27 g of 4-methoxyphenethyl bromide in 100 ml of N,N-dimethylformamide. The mixture is then gradually heated to 100° C., kept at the same temperature for 5 hours and then poured into ice water. The precipitated crystals are filtered, washed with water, ethanol and ether in this order and air-dried. The product is recrystallized from ethanol to obtain 11.8 g of N'-[4-(4-methoxyphenethyloxy)phenyl]-N-methoxy-N-methylurea as white needles, M.P. 100°–101° C.

In the practical usage of the substituted ureas [I], they may be applied as they are or may be applied in any of the formulation forms such as wettable powders, emulsifiable concentrates, granules, dusts and the like.

In preparing such formulation forms, a solid or liquid carrier may be used. As for the solid carrier, there may be mentioned powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like.

As for the liquid carrier, there may be mentioned alcohols (e.g. methyl alcohol, ethyl alcohol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methyl ethyl ketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water, etc.

A surface active agent to be used for emulsification, dispersion and spreading may be any of the nonionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene polymers, oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts, oxyalkylamines and the like. But the surface active agent is not of course limited to these compounds. And, if necessary, gelatin, casein, sodium alginate, starch, agar, polyvinyl alcohol or the like may be used as an auxiliary agent.

Practical embodiments of the herbicidal composition according to the present invention are illustratively shown in the following examples, wherein parts and % are by weight. The Compound Numbers correspond to those in Table 1.

FORMULATION EXAMPLE 1

Eighty parts of Compound No. 1, 5 parts of a surface active agent (polyoxyethylene alkylaryl ether type) and 15 parts of hydrated synthetic silicon dioxide are well mixed while being powdered to obtain a wettable powder formulation.

FORMULATION EXAMPLE 2

Thirty parts of Compound No. 4, 7 parts of a surface active agent (polyoxyethylene alkylaryl ether type), 3 parts of sodium alkylarylsulfonate and 60 parts of xylene are well mixed to obtain an emulsifiable concentrate formulation.

FORMULATION EXAMPLE 3

One part of Compound No. 3, 1 parts of white carbon, 5 parts of sodium lignosulfonate and 93 parts of clay are well mixed while being powdered. The mixture is then well kneaded with the addition of water, granulated and dried to obtain a granular formulation.

FORMULATION EXAMPLE 4

Forty parts of bentonite, 5 parts of sodium lignosulfonate and 55 parts of clay are well mixed while being powdered. The mixture is then well kneaded with the addition of water, granulated and dried to obtain a granule which does not include any active ingredient. To 95 parts of this granule, 5 parts of Compound No. 2 are applied by immersion to obtain a granular formulation.

FORMULATION EXAMPLE 5

Three parts of Compound No. 6, 0.5 part of isopropylphosphate, 66.5 parts of clay and 30 parts of talc are well mixed while being powdered to obtain a dust formulation.

The substituted ureas [I] may be used in admixture with other herbicides to improve the activity as a herbicide, and in some cases, a synergistic effect can be expected. As the other herbicides, there may be mentioned phenoxy herbicides such as 2,4-dichlorophenoxyacetic acid, 2-methyl-4-chlorophenoxyacetic acid and 2,4-dichlorophenoxybutyric acid (including esters and salts thereof); diphenyl ether herbicides such as 2,4-dichlorophenyl-4'-nitrophenyl ether, 2,4,6-trichlorophenyl-4'-nitrophenyl ether, 2,4-dichlorophenyl-4'-nitro-3'-methoxyphenyl ether and 2,4-dichlorophenyl-3'-methoxycarbonyl-4'-nitrophenyl ether; triazine herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine and 2-methylthio-4,6-bisisopropylamino-1,3,5-triazine; triazinone herbicides such as 4-amino-6-tert-butyl-3-methylthio-1,2,4-triazine-5(4H)-one; substituted urea herbicides such as N'-(3,4-dichlorophenyl)-N,N-dimethylurea, N'-(3,4-dichlorophenyl)-N-methoxy-N-methylurea, N'-(3-chloro-4-difluorochloromethylthiophenyl)-N,N-dimethylurea, N'-[4-(4-chlorophenoxy)-phenyl]-N,N-dimethylurea and N'-(α,α,α-trifluoro-m-tolyl)-N,N-dimethylurea; carbamate herbicides such as isopropyl-N-(3-chlorophenyl)carbamate, methyl-N-(3,4-dichlorophenyl)carbamate and 4-chloro-2-butynyl-m-chlorocarbanilate; thiolcarbamate herbicides such as S-(4-chlorobenzyl)-N,N-diethylthiolcarbamate, S-ethyl-N,N-hexamethylenethiolcarbamate and S-ethyl dipropylthiolcarbamate; acid anilide herbicides such as 3,4-dichloropropionanilide, N-methoxymethyl-2,6-diethyl-2-chloroacetanilide and 2-chloro-2',6'-diethyl-N-(butoxymethyl)acetanilide; uracil herbicides such as 5-bromo-3-sec-butyl-6-methyluracil and 3-cyclohexyl-5,6-trimethyleneuracil; pyridinium salt herbicides such as 1,1'-dimethyl-4,4'-bispyridinium dichloride; organophosphorus herbicides such as N-(phosphonomethyl)glycine, O-ethyl-O-(2-nitro-5-methylphenyl)-N-sec-butylphosphoroamidothioate and O-methyl-O-(2-nitro-4-methylphenyl)-N-isopropylphosphoroamidothioate; toluidine herbicides such as α,α,α-trifluoro-2,6-dinitro-N,N-dipropyl-p-toluidine and N-(cyclopropylmethyl)-α,α,α-trifluoro-2,6-dinitro-N-propyl-p-toluidine; N-sec-butyl-4-tert-butyl-2,6-dinitroaniline; 3,5-dinitro-N,N-dipropylsulfanylamide; 5-tert-butyl-3-(2,4-dichloro-5-isopropoxyphenyl)-1,3,4-oxadiazolin-2-one; 3-isopropyl-1H-2,1,3-benzothiadiazine-(4)-3H-one-2,2-dioxide (including salts thereof); α-(β-naphthoxy)propionanilide; 2-(α-naphthoxy)-N,N-diethylpropionamide; 3-amino-2,5-dichlorobenzoic acid, 2-sec-butyl-4,6-dinitrophenol; N-1-naphthylphthalamic acid; 2-(1-allyloxyamino)butylidene-5,5-dimethyl-4-methoxycarbonylcyclohexane-1,3-dione (including salts thereof) and the like. But, the herbicides are not of course limited to these examples.

The herbicides of the present invention may be applied together with fungicides, microbial insecticides, pyrethroid series insecticides, other synthetic insecticides, plant growth regulators or fertilizers.

The concentration of the substituted ureas [I] as the active ingredient in the herbicidal composition is usually from about 1 to 80% by weight, although higher or lower concentrations may be employed.

When the substitutued ureas [I] are applied as a herbicide, the application method and the dosage rate depend upon the type of formulation of the active ingredient, the kinds of crop plants in culture, the kinds of weeds to be killed, the weather conditions, etc. It is preferably applied to both weeds and crop plants over the top in the post-emergence treatment, but it may be applied at any time ranging from the stage immediately after sowing. The dosage rate is generally about 2 to 80 grams, preferably 5 to 40 grams, of the active ingredient per are. For instance, the application to a cultivated land may be carried out to weeds of about 1 to 15 cm in height with a dose of about 2 to 80 grams per are by over-the-top foliar treatment. Further, for instance, the application to a paddy field may be carried out within 4 weeks after the transplantation of the seedlings of rice plants with a dose of the active ingredient in an amount of about 2 to 80 grams per are by water treatment.

The following examples show some typical test data indicating the excellent herbicidal activity of the invention compounds [I]. The Compound Numbers correspond to those in Table 1.

EXAMPLE I

Herbicidal activity and selectivity to soybean of the invention compounds [I] by foliar application:

Plastic pots (35 × 25 × 10 cm) were filled with upland field soil, and the seeds of soybean, cocklebur, radish, redroot pigweed, common lambsquarter, pitchfork, annular morningglory, large crabgrass, goose grass and barnyard grass were sowed in each of the pots and grown for 2 weeks in a greenhouse. The designed amount of the test compound was sprayed to the foliage over the top of the test plants by means of a small hand sprayer. At the time of application, the soybean was at a primary leaf stage; the heights of the cocklebur, radish, redroot pigweed, common lambsquarter, pitchfork and annual morningglory were 2 to 6 cm; and those of the large crabgrass, goose grass and barnyard grass were 4 to 10 cm.

After the spraying, the test plants were placed in the greenhouse for an additional 3 weeks, and the herbicidal activity was evaluated as follows: the aereal parts of the test plants were cut off and weighed (fresh weight); the percentage of the fresh weight of the treated plant to that of the untreated plant was calculated with the latter fresh weight taken as 100; and the crop damage and herbicidal activity were evaluated by the standard given in the table below. The results are shown in Table 2. In the above foliar application, the designed amount of the test compound was formulated into an emulsifiable concentrate, dispersed in water containing a wetting agent and sprayed at a volume of 3 liters per are.

| Rating value | 0 | 1 | 2 | 3 | 4 | 5 |
|---|---|---|---|---|---|---|
| Degree of herbicidal activity | None | Slight (plants recovered from damage) | Low | Moderate | High | Complete death |
| Fresh weight (% of the untreated) | 100 | 99–81 | 80–51 | 50–21 | 20–1 | 0 |

Table 2

| Compound No. | Dosage (weight of active ingredient, g/are) | Evaluation of crop damage and herbicidal activity | | | | | | | | | |
|---|---|---|---|---|---|---|---|---|---|---|---|
| | | Soybean | Cocklebur | Radish | Redroot pigweed | Common lambs-quarter | Pitchfork | Annual morning-glory | Large crab-grass | Goose grass | Barnyard grass |
| 1 | 40 | 1 | 5 | 5 | 5 | 5 | 5 | 5 | 5 | 5 | 5 |
| | 20 | 0 | 5 | 5 | 5 | 5 | 5 | 5 | 5 | 5 | 4 |
| | 10 | 0 | 5 | 5 | 5 | 5 | 5 | 5 | 5 | 4 | 3 |
| | 5 | 0 | 5 | 5 | 5 | 5 | 5 | 5 | 5 | 4 | 3 |
| 2 | 40 | 1 | 5 | 5 | 5 | 5 | 5 | 5 | 5 | 5 | 4 |
| | 20 | 0 | 5 | 5 | 5 | 5 | 4 | 5 | 5 | 4 | 4 |
| | 10 | 0 | 5 | 5 | 5 | 5 | 4 | 5 | 5 | 4 | 4 |
| | 5 | 0 | 5 | 5 | 5 | 5 | 3 | 5 | 4 | 4 | 3 |
| 3 | 20 | 2 | 5 | 5 | 5 | 5 | 5 | 5 | 5 | 5 | 4 |
| | 10 | 0 | 5 | 5 | 5 | 5 | 5 | 5 | 4 | 4 | 4 |
| 4 | 20 | 2 | 5 | 5 | 5 | 5 | 5 | 5 | 5 | 5 | 4 |
| | 10 | 1 | 5 | 5 | 5 | 5 | 5 | 5 | 5 | 4 | 4 |
| 5 | 20 | 0 | 5 | 5 | 5 | 5 | 5 | 5 | 5 | 4 | 4 |
| | 10 | 0 | 5 | 5 | 5 | 5 | 3 | 5 | 5 | 4 | 4 |
| 6 | 20 | 1 | 5 | 5 | 5 | 5 | 5 | 5 | 5 | 5 | 4 |
| | 10 | 0 | 5 | 5 | 5 | 5 | 5 | 5 | 5 | 5 | 4 |
| 7 | 20 | 0 | 5 | 5 | 5 | 5 | 5 | 5 | 5 | 4 | 5 |
| | 10 | 0 | 5 | 5 | 5 | 5 | 5 | 5 | 5 | 4 | 3 |
| 8 | 20 | 1 | 5 | 5 | 5 | 5 | 5 | 5 | 5 | 4 | 4 |
| | 10 | 0 | 5 | 5 | 5 | 5 | 5 | 5 | 5 | 4 | 4 |
| 9 | 40 | 0 | 5 | 5 | 5 | 5 | 5 | 5 | 5 | 5 | 5 |
| | 20 | 0 | 5 | 5 | 5 | 5 | 5 | 5 | 5 | 4 | 4 |
| 10 | 40 | 0 | 5 | 5 | 5 | 5 | 5 | 5 | 5 | 5 | 5 |
| | 20 | 0 | 5 | 5 | 5 | 5 | 5 | 5 | 5 | 5 | 4 |
| N'-[3-Chloro-4-(benzyloxy)-phenyl]-N-methoxy-N-methyl-urea* | 20 | 5 | 5 | 5 | 5 | 5 | 5 | 5 | 5 | 4 | 4 |
| | 10 | 5 | 5 | 5 | 5 | 5 | 4 | 5 | 4 | 4 | 4 |
| Chloroxuron | 40 | 5 | 5 | 5 | 5 | 5 | 5 | 5 | 5 | 5 | 4 |
| | 20 | 3 | 5 | 5 | 5 | 5 | 5 | 5 | 4 | 4 | 3 |
| | 10 | 3 | 5 | 5 | 5 | 5 | 4 | 5 | 2 | 2 | 3 |
| | 5 | 2 | 5 | 5 | 5 | 5 | 4 | 4 | 2 | 1 | 3 |
| Bentazon | 40 | 1 | 5 | 5 | 5 | 5 | 5 | 3 | 1 | 0 | 2 |
| | 20 | 0 | 5 | 5 | 4 | 5 | 5 | 2 | 0 | 0 | 0 |
| | 10 | 0 | 5 | 5 | 3 | 4 | 5 | 2 | 0 | 0 | 0 |
| | 5 | 0 | 5 | 5 | 2 | 3 | 5 | 2 | 0 | 0 | 0 |

Note:
*described in Swiss patent 532,891.

EXAMPLE II

Herbicidal activity and crop selectivity of the invention compounds [I] by foliar application:

Wagner's pots (1/5000 are) were filled with upland field soil, and the seeds of soybean, peanut, corn, rice, cocklebur, black nightshade, sunflower, annual morningglory, smartweed, redroot pigweed, jimsonweed, velvetleaf, green foxtail and goose grass were sowed in separate pots. When the test plants grew to the stages shown in Table 3, the designed amount of the test compound was sprayed to the foliage over the top of the test plants by means of a small hand sprayer.

After the spraying, the test plants were grown for an additional 4 weeks, and damage the crop plants and herbicidal activity against the weeds were evaluated according to the standard given in Example I. The results are shown in Table 3. In the above foliar application, the designed amount of the test compound was formulated into an emulsifiable concentrate, dispersed in water containing a wetting agent and sprayed at a volume of 3 liters per are. The growth stage of each test plant at the time of application is given in Table 3.

Table 3

| Compound No. | Dosage (wt. of active ingredient, g/are) | Soybean 2nd–3rd tri-foliate leaf stage | Peanut 4th tri-foliate leaf stage | Corn 6-7 leaf stage | Rice 4-5 leaf stage | Cocklebur 6 leaf stage | Black nightshade 7 leaf stage | Sunflower 6-8 leaf stage | Annual morning glory 3-4 leaf stage | Smartweed 5 leaf stage | Redroot pigweed 6 leaf stage | Jimsonweed 4 leaf stage | Velvetleaf 5 leaf stage | Green foxtail 5 leaf stage | Goose grass 5 leaf stage |
|---|---|---|---|---|---|---|---|---|---|---|---|---|---|---|---|
| 1 | 30 | 0 | 1 | 1 | 1 | 5 | 5 | 5 | 5 | 5 | 5 | 5 | 5 | 5 | 5 |
| | 20 | 0 | 0 | 0 | 0 | 5 | 5 | 5 | 5 | 5 | 5 | 5 | 5 | 5 | 5 |
| | 10 | 0 | 0 | 0 | 0 | 5 | 5 | 5 | 5 | 5 | 5 | 5 | 5 | 4 | 4 |
| 2 | 30 | 0 | 0 | 1 | 0 | 5 | 5 | 5 | 5 | 5 | 5 | 5 | 5 | 5 | 5 |
| | 20 | 0 | 0 | 0 | 0 | 5 | 5 | 5 | 5 | 5 | 5 | 5 | 5 | 4 | 5 |
| | 10 | 0 | 0 | 0 | 0 | 5 | 5 | 4 | 5 | 4 | 5 | 5 | 5 | 4 | 3 |
| 4 | 30 | 0 | 1 | 1 | 0 | 5 | 5 | 5 | 5 | 5 | 5 | 5 | 5 | 5 | 5 |
| | 20 | 0 | 1 | 0 | 0 | 5 | 5 | 5 | 5 | 5 | 5 | 5 | 5 | 5 | 4 |
| | 10 | 0 | 0 | 0 | 0 | 5 | 5 | 5 | 4 | 5 | 5 | 5 | 5 | 4 | 4 |
| Chloroxuron | 30 | 3 | | | | 5 | 5 | 5 | 5 | 5 | 5 | 5 | 5 | 5 | 5 |
| | 20 | 2 | | | | 5 | 5 | 5 | 5 | 4 | 5 | 5 | 4 | 4 | 3 |
| | 10 | 2 | | | | 5 | 3 | 5 | 4 | 3 | 5 | 5 | 2 | 3 | 3 |
| Bentazon | 30 | 0 | 1 | 0 | 0 | 5 | 5 | 5 | 3 | 5 | 2 | 5 | 5 | 1 | 0 |
| | 20 | 0 | 0 | 0 | 0 | 5 | 4 | 5 | 2 | 5 | 1 | 5 | 5 | 0 | 0 |

Table 3-continued

| | | Evaluation of crop damage and herbicidal activity | | | | | | | | | | | | |
|---|---|---|---|---|---|---|---|---|---|---|---|---|---|---|
| Compound No. | Dosage (wt. of active ingredient, g/are) | Soybean 2nd-3rd trifoliate leaf stage | Peanut 4th trifoliate leaf stage | Corn 6-7 leaf stage | Rice 4-5 leaf stage | Cocklebur 6 leaf stage | Black nightshade 7 leaf stage | Sunflower 6-8 leaf stage | Annual morning glory 3-4 leaf stage | Smartweed 5 leaf stage | Redroot pigweed 6 leaf stage | Jimsonweed 4 leaf stage | Velvetleaf 5 leaf stage | Green foxtail 5 leaf stage | Goosegrass 5 leaf stage |
| | 10 | 0 | 0 | 0 | 0 | 5 | 2 | 5 | 1 | 4 | 0 | 5 | 4 | 0 | 0 |

EXAMPLE III

Herbicidal activity and crop selectivity of the invention compounds [I] by soil application:

Wagner's pots (1/5000 are) were filled with upland field soil, and the seeds of soybean, cotton, corn, wheat, redroot pigweed, common lambsquarter, radish, chickweed and large crabgrass were sowed in separate pots. The designed amount of the test compound formulated into a wettable powder was dispersed in water, and sprayed to the soil surface by means of a small hand sprayer at a volume of 3 liters per are. After the spraying, the test plants were placed in a greenhouse for 3 weeks, and the crop damage and herbicidal activity were evaluated. The evaluation was carried out according to the standard given in Example I. The results are shown in Table 4.

Wagner's pots (1/5000 are) were filled with paddy field soil (1.5 kg/pot) and kept under flooded conditions. Seedlings of rice plants at a three-leaf stage were transplanted thereto, and the seeds of barnyard grass were sowed therein and grown up for 5 days. Thereafter, the designed amount of the test compound was applied to the water layer. Twenty-five days after the application, the evaluation of the herbicidal activity and crop damage was made on the rice plants and the barnyard grass cultivated as well as nutsedge and broad-leaved weeds (e.g. pickerelweed, false pimpernel, toothcup) which emerged spontaneously. The results are shown in Table 5. Herbicidal activity and crop damage were evaluated according to the standard given in Example I. In applying the test compound, its designed amount was formulated into a wettable powder, diluted with water and applied to the water layer at a rate of 15 ml per pot by means of a pipette.

Table 4

| Compound No. | Dosage (weight of active ingredient, g/are) | Evaluation of crop damage and herbicidal activity | | | | | | | | |
|---|---|---|---|---|---|---|---|---|---|---|
| | | Soybean | Cotton | Corn | Wheat | Redroot pigweed | Common lambsquarter | Radish | Chickweed | Large crabgrass |
| 1 | 40 | 0 | 0 | 0 | 1 | 5 | 5 | 5 | 5 | 4 |
| | 20 | 0 | 0 | 0 | 0 | 5 | 5 | 3 | 5 | 3 |
| 2 | 40 | 0 | 1 | 0 | 0 | 5 | 5 | 5 | 5 | 3 |
| | 20 | 0 | 0 | 0 | 0 | 5 | 5 | 3 | 5 | 2 |
| 3 | 40 | 0 | 0 | 0 | 0 | 5 | 5 | 5 | 5 | 3 |
| | 20 | 0 | 0 | 0 | 0 | 5 | 3 | 2 | 4 | 2 |
| 5 | 40 | 0 | 0 | 0 | 0 | 5 | 5 | 5 | 5 | 3 |
| | 20 | 0 | 0 | 0 | 0 | 5 | 4 | 3 | 4 | 3 |

EXAMPLE IV

Herbicidal activity and selectivity to rice of the invention compounds [I] under paddy conditions:

Table 5

| Compound No. | Dosage (weight of active ingredient, g/are) | Evaluation of crop damage and herbicidal activity | | | |
|---|---|---|---|---|---|
| | | Rice plant | Barnyard grass | Broad-leaved weeds | Nutsedge |
| 1 | 20 | 0 | 5 | 5 | 5 |
| | 10 | 0 | 4 | 5 | 5 |
| | 5 | 0 | 4 | 5 | 5 |
| 2 | 20 | 0 | 5 | 5 | 5 |
| | 10 | 0 | 4 | 5 | 5 |
| | 5 | 0 | 3 | 5 | 5 |
| 3 | 20 | 0 | 4 | 5 | 5 |
| | 10 | 0 | 4 | 5 | 5 |
| | 5 | 0 | 3 | 5 | 5 |
| 4 | 20 | 0 | 4 | 5 | 5 |
| | 10 | 0 | 3 | 5 | 5 |
| | 5 | 0 | 3 | 5 | 5 |
| 5 | 20 | 0 | 5 | 5 | 5 |
| | 10 | 0 | 4 | 5 | 5 |
| | 5 | 0 | 3 | 5 | 5 |
| 6 | 20 | 0 | 5 | 5 | 5 |
| | 10 | 0 | 4 | 5 | 5 |
| | 5 | 0 | 3 | 5 | 5 |
| 7 | 20 | 0 | 4 | 5 | 5 |
| | 5 | 0 | 3 | 5 | 5 |
| Control (MCP) | 20 | 3 | 4 | 5 | 5 |

Table 5-continued

| Compound No. | Dosage (weight of active ingredient, g/are) | Evaluation of crop damage and herbicidal activity | | | |
|---|---|---|---|---|---|
| | | Rice plant | Barnyard grass | Broadleaved weeds | Nutsedge |
| 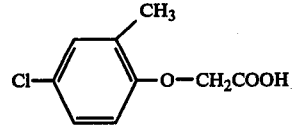 | 10 | 3 | 3 | 5 | 5 |
| | 5 | 1 | 2 | 5 | 5 |

EXAMPLE V

Field trial on herbicidal activity and selectivity to soybean of the invention compounds [I] by foliar application:

The seeds of soybean, sunflower, cocklebur, velvetleaf, annual morningglory, jimsonweed, nightshade, pigweed and smartweed were sowed in each plot under upland field conditions (2 m² per plot, three replications) at the same time. When soybean plants grew to the fourth trifoliate leaf stage, the designed amount of the test compound was sprayed to the foliage over the top of all the test plants by means of a hand sprayer.

After the spraying, the test plants were grown for an additional 16 days, and the crop damage and herbicidal activity were evaluated as follows: the aereal parts of the test plants were cut off and weighed (fresh weight). The percentage of the fresh weight of a treated plant to that of the untreated plant was calculated with the latter fresh weight taken as 100. The results are shown in Table 6. In the above foliar application, the designed amount of the test compound was formulated into a wettable powder, dispersed in water containing a wetting agent and sprayed at a volume of 3 liters per are. The growth stage of each test plant at the time of application is described in Table 6.

Table 6

| Compound No. | Dosage (weight of active ingredient, g/are) | Fresh weight (% of the untreated) | | | | | | | | |
|---|---|---|---|---|---|---|---|---|---|---|
| | | Soybean 4th trifoliate leaf stage | Sunflower 8 leaf stage | Cocklebur 9 leaf stage | Velvetleaf 6-7 leaf stage | Annual morningglory 7-10 leaf stage | Jimsonweed 5 leaf stage | Nightshade 4-5 leaf stage | Pigweed 6-8 leaf stage | Pale smartweed 7-9 leaf stage |
| 1 | 15 | 104 | 0 | 0 | 0 | 0 | 0 | 0 | 0 | 0 |
|  | 10 | 105 | 0 | 0 | 0 | 7 | 0 | 3 | 0 | 1 |
| N'-[3-Chloro-4-benzyloxy)-phenyl]-N-methoxy-N-methylurea | 15 | 37 | 7 | 4 | 10 | 0 | 8 | 5 | 10 | 25 |
|  | 10 | 48 | 24 | 21 | 70 | 15 | 45 | 11 | 21 | 40 |
| Chloroxuron | 15 | 59 | 27 | 3 | 5 | 0 | 3 | 1 | 7 | 7 |
|  | 10 | 81 | 33 | 9 | 48 | 10 | 40 | 5 | 9 | 29 |
| Bentazon | 15 | 103 | 0 | 0 | 0 | 23 | 0 | 85 | 115 | 0 |
|  | 10 | 108 | 0 | 0 | 5 | 47 | 0 | 113 | 132 | 1 |
| Untreated | 0 | 100 | 100 | 100 | 100 | 100 | 100 | 100 | 100 | 100 |

What is claimed is:

1. A compound of the formula

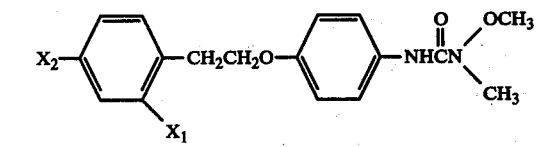

wherein $X_1$ is a hydrogen atom or a methyl group and $X_2$ is a $C_1$-$C_5$ alkyl or a $C_1$-$C_5$ alkoxy group.

2. The compound according to claim 1, wherein $X_1$ is a hydrogen atom and $X_2$ is a methyl group.

3. The compound according to claim 1, wherein $X_1$ and $X_2$ are each a methyl group.

4. The compound according to claim 1, wherein $X_1$ is a hydrogen atom and $X_2$ is a tert-butyl group.

5. A herbicidal composition which comprises as an active ingredient a herbicidally effective amount of the compound according to claim 1 and an inert carrier.

6. The composition according to claim 5, wherein the concentration of the active ingredient is from about 1 to 80% by weight.

7. A method of selectively combating weeds in the cultivation of soybean, peanut, cotton, corn, wheat or rice, which comprises applying a herbicidally effective amount of the compound according to claim 1 to the area wherein the soybean, peanut, corn, cotton, wheat or rice crop is cultivated.

* * * * *